United States Patent [19]

Cheng

[11] 4,220,465

[45] Sep. 2, 1980

[54] IMIDAZOTHIAZINE-1,3(2H)-DIONES

[75] Inventor: Jiin-Duey Cheng, Wilmington, Del.

[73] Assignee: E. I. Du Pont de Nemours and Company, Wilmington, Del.

[21] Appl. No.: 8,853

[22] Filed: Feb. 2, 1979

Related U.S. Application Data

[60] Division of Ser. No. 890,295, Mar. 27, 1978, which is a continuation-in-part of Ser. No. 764,582, Feb. 1, 1977.

[51] Int. Cl.² .................... C07D 279/12; A01N 9/12
[52] U.S. Cl. ........................................ 71/90; 544/58.4
[58] Field of Search ..................... 544/58, 58.4; 71/90

[56] References Cited

U.S. PATENT DOCUMENTS 3,711,448  1/1973  Goodman et al. .................. 544/58.4

Primary Examiner—John M. Ford

[57] ABSTRACT

This invention relates to novel 2-aryl-1H-imidazo-[5,1-c][1,4]thiazine-1,3(2H)-diones, to agricultural compositions containing them and to the method of use of these compounds as pre- or postemergence herbicides for general control of undesirable vegetation. The invention also includes novel intermediate compounds for making the novel compounds.

15 Claims, No Drawings

IMIDAZOTHIAZINE-1,3(2H)-DIONES

RELATED APPLICATIONS

This application is a divisional application of my copending application U.S. Ser. No. 890,295, filed Mar. 27, 1978, which is a continuation-in-part of my copending application U.S. Ser. No. 764,582 filed Feb. 1, 1977.

BACKGROUND OF THE INVENTION

A number of isoindole-type compounds are known in the prior art. Recently, in German Offenlegungsschrift No. 2,165,651 a group of isoindole-1,3-diones was disclosed as herbicides. The general formula for the isoindole-1,3-diones is as follows:

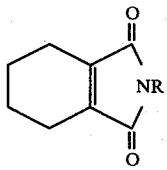

wherein R may be an aryl, aralkyl, or benzyl with optional substituents. U.S. Pat. No. 3,958,976 has disclosed compounds of the following formula as useful for selective weed control in certain crops or for total vegetation control.

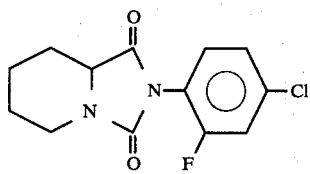

The preparation of 2-phenyl-5,6,8,8A-tetrahydro-1H-imidazo[5,1-c][1,4]thiazine-1,3(2H)-dione has been reported in J Med Pharm Chem 2 553 (1960) and J Chem Soc, Perkin I, 132 (1973). The synthesis of 3-carbethoxy-4-phenylaminocarbonyl-5,6-dihydrothiazine has been reported in Gazz. Chin. Ital., 92, 1367 (1962). No agricultural utility was disclosed for either of these compounds. It has now been found that placing proper substituents(s) on the benzene ring in this class of compounds significantly enhances their herbicidal activity.

SUMMARY OF THE INVENTION

This invention relates to novel compounds of Formulae Ia, Ib and Ic to agricultural compositions containing them and to the method of use of these compounds as pre- or post-emergence herbicides for the general control of undesired vegetation. The invention also includes the novel intermediates of Formula Id.

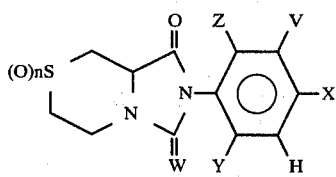

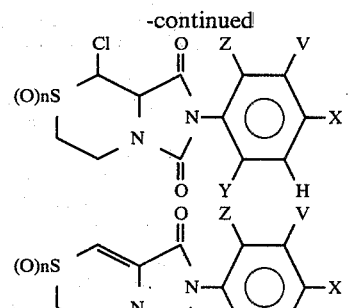

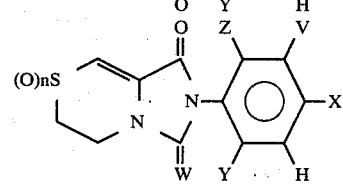

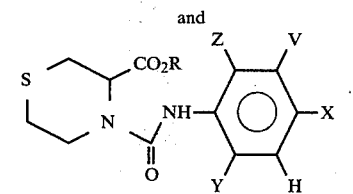

where
n is 0, 1 or 2;
W is oxygen or sulfur;
X is hydrogen, fluorine, chlorine, bromine, cyano, methyl, methoxy or nitro;
Y is hydrogen, fluorine, chlorine or methyl;
Z is hydrogen, fluorine or methyl;
V is hydrogen, fluorine, chlorine or OR; and
R is propargyl or alkyl of 1 to 4 carbon atoms with the proviso that (1) X, Y, Z and V cannot all be hydrogen when n is 0 and W is oxygen; (2) when V is other than H, at least one of X, Y and Z must be other than H; and (3) n is 0 when W is sulfur for compounds of Formula Ic.

Preferred for their high herbicidal activity are those compounds of Formulae Ia, Ib and Ic where, independently,
(a) n is 1 or 2;
(b) W is oxygen;
(c) X is fluorine, chlorine, bromine or cyano;
(d) Y is hydrogen, fluorine or chlorine;
(e) Z is hydrogen or fluorine; or
(f) V is hydrogen, fluorine or chlorine or OR where R is alkyl of 1 to 3 carbon atoms with the proviso that when V is other than H, at least one of X, Y and Z must be other than H.

More preferred for their higher herbicidal activity are those compounds of Formulae Ia, Ib and Ic where n is 2, X is fluorine, chlorine or bromine, Y is hydrogen, fluorine or chlorine, V is hydrogen or alkoxy of 1-3 carbons and Z is hydrogen, provided X and Y are chlorine when V is alkoxy of 1-3 carbons.

Specifically preferred for their outstanding herbicidal activity are:
(1) 2-(4-chloro-2-fluorophenyl)-5,6,8,8A-tetrahydro-1H-imidazo[5,1-c][1,4]thiazine-1,3(2H)-dione-7,7-dioxide, m.p. 224°–226° C.;
(2) 2-(4-chlorophenyl)-5,6,8,8A-tetrahydro-1H-imidazo[5,1-c][1,4]thiazine-1,3(2H)-dione-7,7-dioxide, m.p. 255°–257° C.;
(3) 2-(3,4-dichlorophenyl)-5,6,8,8A-tetrahydro-1H-imidazo[5,1-c][1,4]thiazine-1,3(2H)-dione-7,7-dioxide, m.p. 234°–236° C.;

(4) 2-(4-chloro-2-fluorophenyl)-5,6-dihydro-1H-imidazo[5,1-c][1,4]thiazine-1,3(2H)-dione-7,7-dioxide, m.p. 187.5°–189° C.

(5) 2-(2,4-dichloro-5-methoxyphenyl)-5,6,8,8A-tetrahydro-1H-imidazo[5,1-c][1,4]thiazine-1,3(2H)-dione-7,7-dioxide, m.p. 246°–247.5° C.

(6) 2-(2,4-dichloro-5-isopropoxyphenyl)-5,6,8,8A-tetrahydro-1H-imidazo[5,1-c][1,4]thiazine-1,3(2H)-dione-7,7-dioxide, m.p. 196°–199° C.

(7) 2-(4-chloro-2-fluorophenyl)-8-chloro-5,6,8,8A-tetrahydro-1H-imidazo[5,1-c][1,4]thiazine-1,3(2H)-dione-7,7-dioxide, m.p. 250°–252° C. 2-(2,4-dichloro-5-methoxyphenyl)-8-chloro-5,6,8,8A-tetrahydro-1H-imidazo[5,1-c][1,4]thiazine-1,3(2H)-dione-7,7-dioxide, m.p. 228.5°–229.5°.

DETAILED DESCRIPTION OF THE INVENTION

Synthesis of the compounds

The novel compounds of Formula Ia can be prepared as shown in Scheme I:

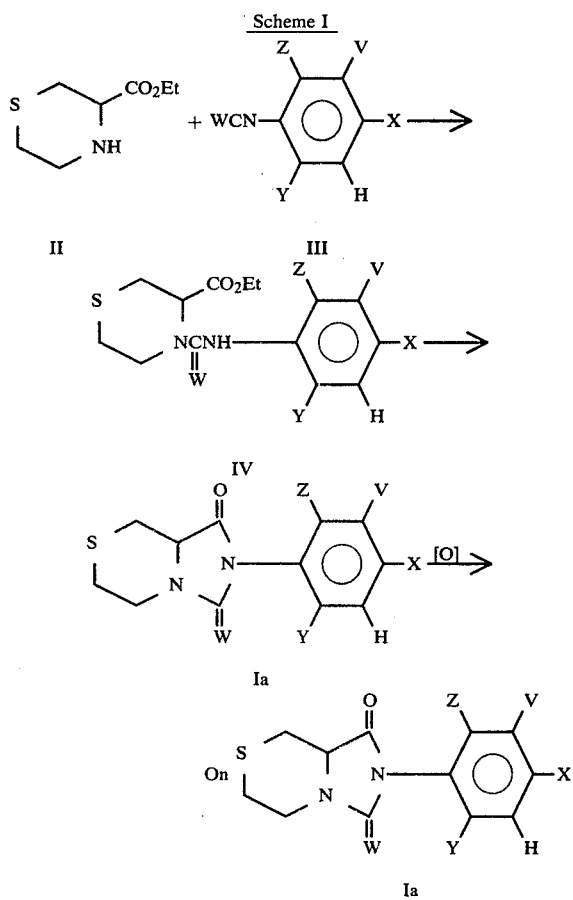

Preparation of compounds of Formula Ia requires the use of a thiomorpholine-3-carboxylate such as 3-carbethoxythiomorpholine (II). Compound II can be synthesized by the reaction of 2-aminoethanethiol and ethyl 2,3-dibromopropionate in a mixture of benzene and chloroform as reported in J. Chem. Soc. Perkin II, 203 (1976).

The reaction of a thiomorpholine-3-carboxylate and an aryl isocyanate or isothiocyanate of Formula III can be carried out in various aprotic solvents or in water/organic solvent combinations under atmospheric pressure. The reaction takes place at 0° to 100° C. in 10 minutes to several hours. For convenience the preparation of compounds of Formula IV is carried out in hexanes or a mixture of hexanes and ether at 10° to 30° C. over a period of one to three hours. The product is precipitated and collected by filtration. In some instances, ring closure to compounds of Formula Ia occurs too rapidly for IV to be isolated.

The cyclization of compounds of Formula IV to compounds of Formula Ia is an acid-catalyzed reaction [J. Med. Pharm. Chem. 2, 553 (1960); J. Chem. Soc. Perkin I, 132 (1973)] as well as a base catalyzed reaction. The above cited references disclose the preparation of 2-phenyl-5,6,8,8A-tetrahydro-1H-imidazo[5,1-c][1,4]thiazine-1,3(2H)-dione (Ia: W=O; X=Y=Z=V=H; n=0) in an acidic medium. It has now been found that ring closure can also be effectively promoted by the presence of catalytic amounts of base, e.g. metal hydroxide or metal alkoxide. In general, cyclization of compounds of Formula IV can be carried out in either protic or aprotic solvents at 0° to 150° C. under atmospheric pressure for 10 minutes to 20 hours. It is preferred that the reaction be carried out in refluxing methanol or ethanol for 10 minutes to 2 hours. The sulfides of Formula Ia, where W=oxygen, can be selectively oxidized to sulfoxides or sulfones of Formula Ia by using stoichiometric amounts of oxidizing agents such as peroxyacetic acid or m-chloroperoxybenzoic acid in an inert solvent such as methylene chloride or chloroform at 0° to 40° C. It is preferred to run the reaction in methylene chloride at 5° to 25° C. for 2 to 5 hours.

The sulfoxides of Formula Ia where W=sulfur can be prepared by selective oxidation of the sulfides with a suitable oxidizing agent such as m-chloroperoxybenzoic acid usually at 0° to 10° C.

The sulfones of Formula Ia in which W is sulfur can be prepared by the reaction of aryl isothiocyanate and 3-carbethoxythiomorpholine-1,1-dioxide (V). Intermediate VI undergoes ring closure rapidly under reaction conditions. Compound V can be prepared by selective oxidation of a corresponding hydrochloride salt of II at −5° to 15° C. The reaction sequences of this preparation is illustrated by Scheme II in which Ar designates the aromatic ring of Formula Ia:

Scheme II

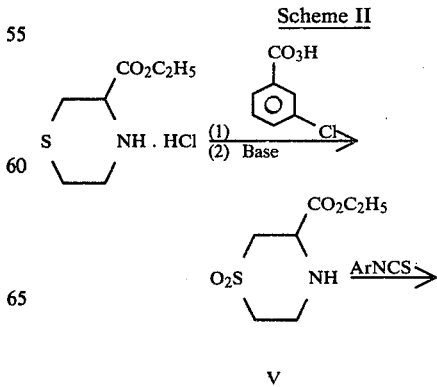

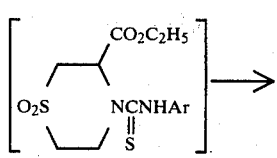

VI

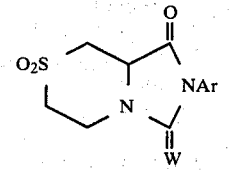

Ia (W = S, n = 2)

Compounds of Formula Ib can be prepared by two different pathways as shown by Scheme III.

Scheme III

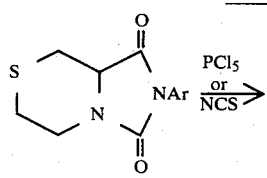

Ia

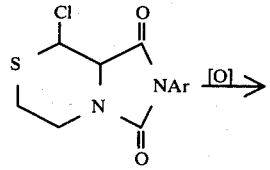

Ib(n = 0)

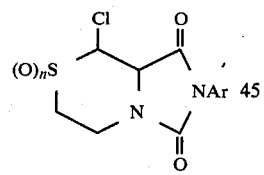

Ib(n = 1,2)

The reaction of a sulfide of Ia and phosphorus pentachloride takes place at room temperature to give Ib (n=0). For practical purposes, the chlorination reaction is carried out under reflux in chloroform for one to five hours. The product Ib can be isolated and purified by recrystallization. The sulfide of Ib can also be conveniently prepared by treatment at room temperature of Ia (n=0) with N-chlorosuccinimide (NCS) in a chlorinated solvent such as methylene chloride, carbon tetrachloride or chloroform.

Compounds of formula Ic can be prepared from those of formula Ib by elimination of hydrogen chloride as shown in Scheme IV. Elimination occurs in neutral dimethylsulfoxide, or in other suitable solvents, such as chloroform, when base catalyzed. Generally, organic as well as inorganic bases are sufficient to promote the formation of Ic from Ib. Dialkylarylamines or trialkylamines such as triethylamine are preferred.

SCHEME IV

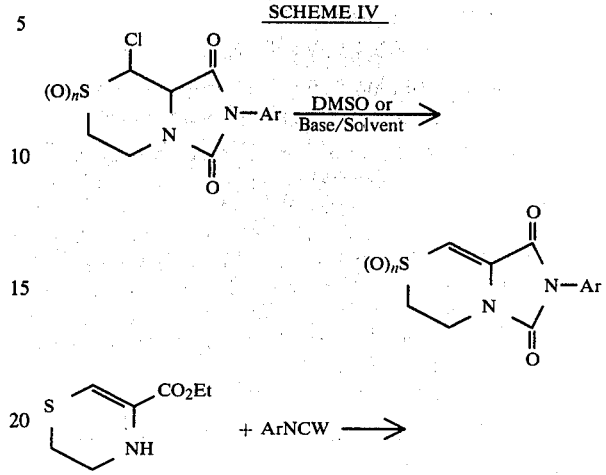

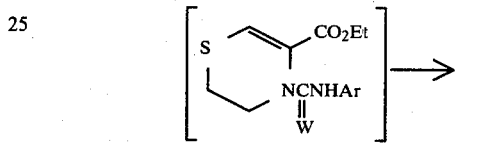

VII

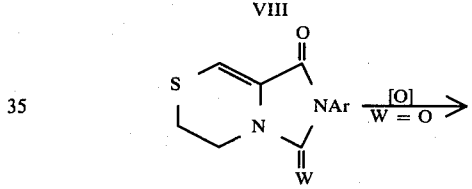

VIII

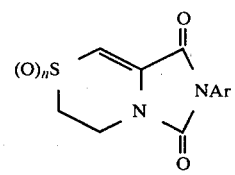

Ib

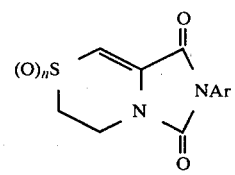

Ib

An alternative pathway to prepare Ib is the reaction of an arylisocyanate or arylisothiocyanate with 5,6-dihydro-1,4-thiazine-3-carboxylate under the conditions that compounds Ia were prepared. Compound VII can be synthesized by the reaction of 2-aminoethanethiol and bromopyruvate [Gazz. Chim. Ital., 92, 1367 (1962)]. The reaction of compound VII and an arylisocyanate or arylisothiocyanate takes place instantaneously in ether or a mixture of ether and hexanes. The intermediate ureas (VIII) need not be isolated. The reaction mixture is allowed to stand at ambient temperature for 3 to 24 hours. The product usually crystallizes from solution and can be collected by filtration.

The corresponding sulfones and sulfoxides of Ib and Ic (W=O) are prepared by selective oxidation of the sulfides of Ib and Ic by a suitable oxidizing agent such as m-chloroperoxybenzoic acid.

The preparation of compounds in the present invention can be more clearly demonstrated by the following specific examples.

EXAMPLE 1

3-Carbethoxy-4-(4-chloro-2-fluorophenylaminocarbonyl)thiomorpholine

An emulsion of 14 g of 3-carbethoxythiomorpholine in 50 ml of n-hexane was added dropwise to a solution of 14 g of 4-chloro-2-fluorophenylisocyanate in 60 ml of anhydrous ether at 15° to 28° C. with stirring. A heavy oil formed after the addition. The oil crystallized after stirring at room temperature for 15 min. The precipitate was collected by filtration to give 24.3 g of 3-carbethoxy-4-(4-chloro-2-fluorophenylaminocarbonyl)thiomorpholine, m.p. 111.5°–112.5° C.

The following compounds of this type can be prepared by using the procedure of Example 1.

[Structure: thiomorpholine with CO₂Et group, N—C(=O)—NH—phenyl with substituents X, Y, Z, V]

| X | Y | Z | V | Melting Point °C. |
|---|---|---|---|---|
| Cl | H | H | H | 152.5°–154.5° |
| Cl | Cl | H | H | 94°–96° |
| CH₃O | H | H | H | 144°–146° |
| CH₃ | H | H | H | 134°–135.5° |
| F | H | H | H | 110°–114° |
| H | F | H | H | 97°–101° |
| H | Cl | H | Cl | 124.5°–125.5° |
| CH₃ | CH₃ | CH₃ | H | 153.5°–155° |
| Br | H | H | H | |
| Br | F | H | H | 119°–122° |
| Cl | Cl | H | CH₃O | 83°–85° |
| Cl | Cl | H | i-PrO | |
| Cl | H | H | Cl | |
| F | F | H | H | |
| CH₃O | Cl | H | H | |
| H | F | F | H | |
| CN | H | H | H | |
| Cl | Cl | H | n-BuO | |
| H | Cl | H | F | |
| Cl | Cl | H | Cl | 125°–131° |
| H | CH₃ | CH₃ | H | 173°–175° |
| NO₂ | Cl | H | H | 135°–137.5° |
| Cl | Cl | H | CH≡C—CH₂O— | |

EXAMPLE 2

2-(4-Chlorophenyl)-5,6,8,8A-tetrahydro-1H-imidazo[5,1-c][1,4]-thiazine-1,3(2H)-dione Seven grams of 3-carbethoxythiomorpholine and 6.5 g of 4-chlorophenyl isocyanate were added to 60 ml of hexanes containing 10 drops of triethylamine as a catalyst. A mild exothermic reaction took place as the reactants mixed. After the mixture cooled to room temperature, the precipitate was collected by filtration and recrystallized from a mixture of methylene chloride and ether to give 4 g of 3-carbethoxy-4-(4-chlorophenylaminocarbonyl)thiomorpholine, mp 152.5°–154.5° C.

The mother liquors were combined and evaporated to dryness. The residue was refluxed with 0.5 g of sodium methoxide in 50 ml of methanol for 1.5 hr. On cooling, the precipitate was collected by filtration to give 4.8 g of 2-(4-chlorophenyl)-5,6,8,8A-tetrahydro-1H-imidazo[5,1-c][1,4]thiazine-1,3(2H)-dione, mp 178.5°–180° C.

EXAMPLE 3

2-(4-Chlorophenyl)-5,6,8,8A-tetrahydro-1H-imidazo[5,1-c][1,4]-thiazine-1,3(2H)-dione-7-oxide A solution of 2.8 g of m-chloroperoxybenzoic acid in 30 ml of methylene chloride was added dropwise to a solution of 3.8 g of 2-(4-chlorophenyl)-5,6,8,8A-tetrahydro-1H-imidazo[5,1-c][1,4]thiazine-1,3(2H)-dione in 40 ml of methylene chloride at 0° to 5° C. The resulting suspension was stirred in an ice bath for 3 hr. At the end of the reaction time, the suspension was washed with two portions of 80 ml of saturated sodium bicarbonate solution, washed once with 50 ml of water, dried over anhydrous magnesium sulfate and filtered. The filtrate was concentrated in a rotary evaporator to remove solvent. The residue was crystallized from a mixture of methylene chloride and ether to give 3 g of 2-(4-chlorophenyl)-5,6,8,8A-tetrahydro-1H-imidazo[5,1-c][1,4]thiazine-1,3(2H)-dione-7-oxide, m.p. 195.5°–205° C. Recrystallization from 98:2 ethanol/benzene gave m.p. 203°–205° C. Molecular weight, as determined by mass spectrometry (M+), is 298. The mass spectral pattern indicated one chlorine atom to be present.

EXAMPLE 4

2-(2-Fluoro-4-chlorophenyl)-5,6,8,8A-tetrahydro-1H-imidazo[5,1-c][1,4]thiazine-1,3(2H)-dione A solution of 7.5 g of 2-fluoro-4-chlorophenyl isocyanate in 30 ml of hexanes was added dropwise to a stirred solution of 7.8 g of 3-carbethoxythiomorpholine and 10 drops of triethylamine in 30 ml of hexanes. An exothermic reaction took place and a heavy oil formed during the addition. As the mixture cooled to room temperature the oil crystallized. The suspension was kept at ambient temperature for 2½ days. The precipitate was collected by filtration to give 11.4 g of 2-(2-fluoro-4-chlorophenyl)-5,6,8,8A-tetrahydro-1H-imidazo[5,1-c][1,4]thiazine-1,3(2H)-dione, mp 138°–141° C.

EXAMPLE 5

2-(2-Fluoro-4-chlorophenyl)-5,6,8,8A-tetrahydro-1H-imidazo[5,1-c][1,4]thiazine-1,3(2H)-dione-7,7-dioxide A solution of 5.6 g of m-chloroperoxybenzoic acid in 60 ml of methylene chloride was added dropwise to a solution of 2-(2-fluoro-4-chlorophenyl)-5,6,8,8A-tetrahydro-1H-imidazo[5,1-c][1,4]thiazine-1,3(2H)-dione in 40 ml of methylene chloride at 0°–10° C. and then stirred at ambient temperature for 5.5 hr. The solution was extracted with two 50 ml portions of saturated sodium bicarbonate solution, washed once with 50 ml of water, dried over anhydrous magnesium sulfate, and filtered. The filtrate was concentrated and diluted with ethanol to give 3.3 g of 2-(2-fluoro-4-chlorophenyl)-5,6,8,8A-tetrahydro-1H-imidazo[5,1-c][1,4]thiazine-1,3(2H)-dione-7,7-dioxide, mp 224°–226° C.

EXAMPLE 6

2-(4-Chlorophenyl)-2,3,5,6,8,8A-hexahydro-3-thioxo-1H-imidazo[5,1-c][1,4]thiazine-1-one-7,7-dioxide Three ml of concentrated HCl was added to a cold solution of 5 g of 3-carbethoxythiomorpholine in 100 ml of methylene chloride. The mixture was stirred at room temperature for 30 min. The solution was cooled in an ice bath and 11.6 g of m-chloroperoxybenzoic acid was added in portions. After stirring at 0° to 5° C. for 3 hr., the suspension was made alkaline with 50% potassium carbonate solution. Suspended m-chlorobenzoic acid was removed by filtration. The filtrate was extracted once with each of 80 ml of saturated sodium bicarbonate solution, 80 ml of water, dried over anhydrous magnesium sulfate and filtered. The filtrate was then evaporated to give 2.3 g of crude 3-carbethoxythiomorpholine-1,1-dioxide as a yellow oil.

A solution of 1.9 g of 4-chlorophenyl isothiocyanate in 20 ml of ether was added dropwise to a solution of 2.3 g of crude 3-carbethoxythiomorpholine-1,1-dioxide in a mixture of 40 ml of ether and 20 ml of methylene chloride. The mixture was stirred at room temperature for 1.5 hr. Solvent was removed by a rotary evaporator. The oil was crystallized from methylene chloride - ether to give 2-(4-chlorophenyl)-2,3,5,6,8,8A-hexahydro-3-thioxo-1H-imidazo[5,1-c][1,4]thiazine-1-one-7,7-dioxide, mp 215°–217° C. Recrystallization from ethanol-methylene chloride gave 0.6 g, mp 222.5°–224° (dec.).

Other useful compounds of this invention that can be prepared by the preceding procedures include the following examples.

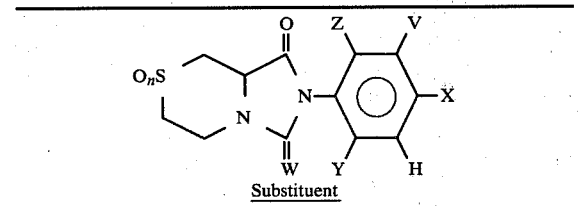

| | | | Substituent | | | |
|---|---|---|---|---|---|---|
| X | Y | Z | V | W | n | Melting Point °C. |
| Cl | H | H | H | 0 | 2 | 255°–257° |
| Cl | F | H | H | 0 | 1 | 218°–221° |
| Cl | H | H | Cl | 0 | 0 | 154°–156° |
| Cl | H | H | Cl | 0 | 2 | 234°–236° |
| Cl | Cl | H | H | 0 | 0 | 112°–114° |
| Cl | Cl | H | H | 0 | 2 | 202°–205° |
| H | CH$_3$ | H | H | 0 | 0 | |
| H | CH$_3$ | H | H | 0 | 2 | |
| H | F | F | H | 0 | 2 | |
| CH$_3$ | CH$_3$ | CH$_3$ | H | 0 | 2 | 124°–125° |
| CH$_3$ | CH$_3$ | CH$_3$ | H | 0 | 0 | 172°–172.5° |
| H | F | H | H | 0 | 2 | |
| Br | H | H | H | 0 | 2 | |
| CN | H | H | H | 0 | 2 | |
| CH$_3$O | H | F | H | 0 | 2 | |
| Cl | Cl | H | CH≡CCH$_2$O | 0 | 0 | |
| Cl | Cl | H | CH≡CCH$_2$O | 0 | 2 | |
| Cl | H | H | H | S | 0 | 215°–217° |
| Cl | F | H | H | S | 0 | 152.5°–153.5° |
| CN | F | H | H | 0 | 2 | |
| NO$_2$ | H | H | H | 0 | 0 | 171°–173° |
| NO$_2$ | H | H | H | 0 | 2 | 270°–273° (dec.) |
| Cl | Cl | H | i-C$_3$H$_7$O | 0 | 2 | 196°–199° |
| Cl | Cl | H | i-C$_3$H$_7$O | 0 | 1 | |
| Cl | Cl | H | i-C$_3$H$_7$O | 0 | 0 | 130°–133° |
| Cl | Cl | H | i-C$_3$H$_7$O | S | 2 | |
| H | Me | Me | H | 0 | 0 | 135°–136.5° |
| H | Me | Me | H | 0 | 2 | 207.5°–209.5° |
| Cl | Cl | H | OCH$_3$ | 0 | 2 | 246°–247.5° |
| Cl | Cl | H | OCH$_3$ | 0 | 1 | |
| Cl | Cl | H | OCH$_3$ | 0 | 0 | 125°–130° |
| Cl | Cl | H | n-C$_4$H$_9$O | 0 | 2 | |
| F | F | F | H | 0 | 2 | |
| NO$_2$ | F | H | H | 0 | 2 | |
| Cl | Cl | H | OCH$_3$ | S | 0 | |
| Cl | H | H | F | 0 | 2 | |
| Cl | H | H | H | S | 1 | 199°–200.5° |
| Cl | F | H | H | S | 1 | 214°–215° (dec.) |
| Cl | F | H | H | S | 2 | 203.5°–204° (dec.) |
| CH$_3$O | H | H | H | 0 | 0 | 182°–184° |
| CH$_3$O | H | H | H | 0 | 2 | 206°–209° |
| Cl | CH$_3$ | H | H | 0 | 2 | 198°–200° |

-continued

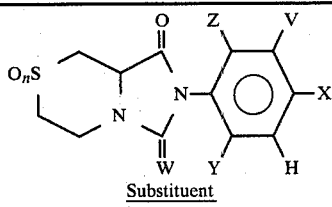

| | | | Substituent | | | |
|---|---|---|---|---|---|---|
| X | Y | Z | V | W | n | Melting Point °C. |
| Cl | CH$_3$ | H | H | 0 | 0 | 143°–145° |
| NO$_2$ | Cl | H | H | 0 | 0 | 205°–207.5° |
| NO$_2$ | Cl | H | H | 0 | 2 | 254°–255° |
| Cl | Cl | H | Cl | 0 | 0 | 142°–144.5° |
| Cl | Cl | H | Cl | 0 | 2 | 214°–216.5° |
| Br | F | H | H | 0 | 0 | 132°–135° |
| Br | F | H | H | 0 | 1 | 203°–209° |
| Br | F | H | H | 0 | 2 | 228°–230° |
| CH$_3$ | H | H | H | 0 | 0 | 196°–198° |
| CH$_3$ | H | H | H | 0 | 2 | 222°–224° |
| F | H | H | H | 0 | 0 | 160°–162° |
| F | H | H | H | 0 | 2 | 223°–228° |
| Cl | Cl | H | H | S | 0 | 158.5°–160° |
| H | Cl | H | Cl | 0 | 0 | 165.5°–168° |
| H | Cl | H | Cl | 0 | 2 | 216°–218° |

EXAMPLE 7

2-(4-Chlorophenyl)-5,6,8,8A-tetrahydro-8-chloro-1H-imidazo[5,1-c][1,4]thiazine-1,3(2H)-dione and 2-(4-chlorophenyl)-5,6-dihydro-1H-imidazo[5,1-c][1,4]thiazine-1,3(2H)-dione To a solution of 14 g of phosphorous pentachloride in 150 ml of chloroform was added 15.7 g of 2-(4-chlorophenyl)-5,6,8,8A-tetrahydro-1H-imidazo[5,1-c][1,4]thiazine-1,3(2H)-dione. The solution was refluxed 1.5 hr under anhydrous conditions, cooled to room temperature and neutralized by addition of saturated sodium bicarbonate solution. The chloroform layer was separated, extracted with 50 ml each of saturated sodium bicarbonate solution and water. The chloroform solution was then dried over anhydrous magnesium sulfate. and filtered. The filtrate was concentrated and diluted with ether to give 12 g of crude material which was shown by NMR to contain about 50% starting material. Recrystallization from chloroform gave 3 g of 2-(4-chlorophenyl)-5,6,8,8A-tetrahydro-8-chloro-1H-imidazo[5,1-c][1,4]thiazine-1,3(2H)-dione, m.p. 144°–145.5° (dec.). The structure was confirmed by $^{13}$C NMR spectroscopy.

The mother liquors were combined and evaporated. The residue was refluxed with 7 g of phosphorous pentachloride in 75 ml of chloroform for 1 hr. To the mixture, 5 ml of triethylamine was added and refluxed for an additional 3 hrs. On cooling, the solution was extracted with two 100 ml portions of 5% sodium hydroxide solution, 100 ml of water, dried over anhydrous magnesium sulfate and filtered. The filtrate was concentrated and diluted with ether to give 8.4 g of 2-(4-chlorophenyl)-5,6-dihydro-1H-imidazo[5,1-c][1,4]thiazine-1,3(2H)-dione, m.p. 155°–157.5° C.

EXAMPLE 8

8-Chloro-2-(4-chloro-2-fluorophenyl)-5,6,8,8A-tetrahydro-1H-imidazo[5,1-c][1,4]thiazine-1,3(2H)-dione To a solution of 4.4 g of 2-(4-chloro-2-fluorophenyl)-5,6,8,8A-tetrahydro-1H-imidazo[5,1-c][1,4]thiazine-1,3(2H)-dione in 100 ml of methyl chloride was added 2 g of N-chlorosuccinimide. The resulting suspension was stirred at room temperature for 4 hours and filtered. The filtrate was concentrated and diluted with ether. The precipitate was collected by filtration, washed thoroughfully with water, and air-dried to give 4.1 g of 8-chloro-2-(4-chloro-2-fluorophenyl)-5,6,8,8A-tetrahydro-1H-imidazo[5,1-c][1,4]thiazine-1,3-(2H)-dione, m.p. 108°–109° (dec.).

EXAMPLE 9

8-Chloro-2-(4-chloro-2-fluorophenyl)-5,6,8,8A-tetrahydro-1H-imidazo[5,1-c][1,4]thiazine-1,3(2H)-dione-7,7-dioxide m-Chloroperoxybenzoic acid (2.6 g) was added in portions to a cold solution of 2.1 g of 8-chloro-2-(4-chloro-2-fluorophenyl)-5,6,8,8A-tetrahydro-1H-imidazo[5,1-c][1,4]thiazine-1,3(2H)-dione in 30 ml of methylene chloride. The mixture was stirred on an ice bath for 3.5 hours and then sufficient amount of saturated sodium bicarbonate solution to effect precipitation was added with stirring. The resulting precipitate was collected by filtration, washed with water, and air-dried to give 1.0 g of 8-chloro-2-(4-chloro-2-fluorophenyl)-5,6,8,8A-tetrahydro-1H-imidazo[5,1-c][1,4]thiazine-1,3(2H)-dione-7,7-dioxide, m.p. 250°–252°.

Useful compounds that can be prepared by the preceding procedures include the following examples:

| X | Y | Z | V | n | melting point °C. |
|---|---|---|---|---|---|
| Cl | F | H | H | 1 | 219.5°–221° (dec.) |
| Cl | Cl | H | OCH3 | 0 | 201°–203° |
| Cl | Cl | H | OCH3 | 2 | 228.5°–229.5° |
| Cl | Cl | H | OCH3 | 1 | |
| Br | F | H | H | 0 | |
| Br | F | H | H | 1 | |
| Br | F | H | H | 2 | |
| Cl | H | H | H | 2 | |
| Cl | Cl | H | i-C3H7O | 0 | |
| Cl | Cl | H | i-C3H7O | 2 | |
| Cl | Cl | H | Cl | 0 | |
| Cl | Cl | H | Cl | 2 | |
| Cl | H | H | Cl | 0 | |
| Cl | H | H | Cl | 2 | |
| Cl | Cl | H | CH≡CCH2O— | 0 | |
| Cl | Cl | H | CH≡CCH2O— | 2 | |

EXAMPLE 10

2-(4-Chloro-2-fluorophenyl)-5,6-dihydro-1H-imidazo[5,1-c][1,4]-thiazine-1,3(2H)-dione A solution of 8.6 g of 4-chloro-2-fluorophenylisocyanate in 20 ml of anhydrous ether was added dropwise to a mixture of 9.8 g of crude 3-carbethoxy-5,6-dihydro-1,4-thiazine and 10 drops of triethylamine in 20 ml of ether. After the addition, 30 ml of hexane was added dropwise in 20 min. The solution was stirred at room temperature for 3 hrs. The solution was concentrated in vacuo to remove solvent. The resulting oil was crystallized from ether to give 10 g of 2-(4-chloro-2-fluorophenyl)-5,6-dihydro-1H-imidazo[5,1-c][1,4]thiazine-1,3(2H)-dione, m.p. 117.5°–120.5° C.

Useful compounds that can be prepared by the preceding procedures include the following:

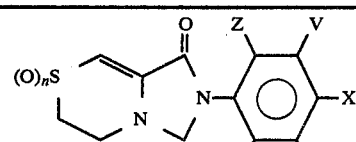

| X | Y | Z | V | W | n | Melting Point °C. |
|---|---|---|---|---|---|---|
| Cl | H | H | H | | 0 | 1 | 206°–208° |
| Cl | H | H | H | | 0 | 2 | 239°–240° |
| Cl | H | H | H | S | 0 | 184°–185.5° |
| Cl | H | H | Cl | | 0 | 0 | 171°–173° |
| Cl | H | H | Cl | | 0 | 2 | 227.5°–229° |
| Cl | F | H | H | | 0 | 2 | 187.5°–189° |
| Cl | F | H | H | | 0 | 1 | 174°–175° |
| Cl | F | H | H | S | 0 | | 134°–137° |
| Cl | Cl | H | H | S | 0 | | 130°–132° |
| Cl | Cl | H | H | | 0 | 0 | 143°–144.5° |
| Cl | Cl | H | H | | 0 | 1 | 226°–228° |
| Cl | Cl | H | H | | 0 | 2 | 244°–245° |
| H | Cl | H | Cl | | 0 | 0 | 183°–185° |
| H | Cl | H | Cl | | 0 | 1 | 204.5°–205.5° |
| H | Cl | H | Cl | | 0 | 2 | 253°–255° (dec.) |
| Cl | Cl | H | CH3O | | 0 | 0 | 203°–205° |
| Cl | Cl | H | CH3O | | 0 | 1 | 167°–171° |
| Cl | Cl | H | CH3O | | 0 | 2 | 203°–205° |
| Cl | Cl | H | i-Pro | | 0 | 0 | |
| Cl | Cl | H | i-Pro | | 0 | 1 | |
| Cl | Cl | H | i-Pro | | 0 | 2 | |
| Cl | Cl | H | n-Buo | | 0 | 1 | |
| F | F | H | F | | 0 | 1 | |
| Br | H | H | H | | 0 | 1 | |
| Br | F | H | H | S | 0 | | |
| Br | F | H | H | | 0 | 0 | |
| Br | F | H | H | | 0 | 1 | |
| Br | F | H | H | | 0 | 2 | |
| F | F | F | H | | 0 | 2 | |
| CH3 | CH3 | CH3 | H | | 0 | 2 | |
| CH3 | CH3 | H | H | | 0 | 2 | |
| CH3O | Cl | H | H | | 0 | 0 | |
| CH3O | Cl | H | H | | 0 | 1 | |
| CH3O | Cl | H | H | | 0 | 2 | |
| CN | H | H | H | | 0 | 1 | |
| NO2 | H | F | H | | 0 | 2 | |
| Cl | Cl | H | CH≡CCH2O | | 0 | 0 | |
| Cl | Cl | H | CH≡CCH2O | | 0 | 2 | |

Useful formulations of the compounds of Formulae Ia and Ib can be prepared in conventional ways. They include granules, pellets, solutions, suspensions, emulsions, wettable powders, emulsifiable concentrates and the like. Many of these may be applied directly to the plants. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Granules and Pellets | 1–95 | 5–99 | 0–15 |
| High Strength | | | |

| | Percent by Weight | | |
|---|---|---|---|
| | Active Ingredient | Diluent(s) | Surfactant(s) |
| Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd. Edn., Dorland Books, Caldwell, N.J. The more absorptive diluents are preferred for wettable powders. Typical liquid diluents and solvents are described in Marsden, "Solvents Guide," 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual," MC Publishing Co., Ridgewood, N.J., as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made of spraying the active material upon preformed granular carries or by agglomeration techniques. See J. E. Browning, "Agglomeration," *Chemical Engineering*, Dec. 4, 1967, pp. 147ff. and "Perry's Chemical Engineer's Handbook," 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62 and Ex. 8, 12, 15, 39, 41, 52, 53, 58, 132, 138–140, 162–164, 166, 167, 169–182.

H. Gysin and E. Knüsli, U.S. Pat. No. 2,891,855, June 23, 1959, Col. 3, Line 66 through Col. 5, Line 17 and Examples 1–4.

G. C. Klingman, "Weed Control as a Science," John Wiley & Sons, Inc., New York, 1961, pp. 81–96.

J. D. Fryer and S. A. Evans, "Weed Control Handbook," 5th Edn. Blackwell Scientific Publications, Oxford, 1968, pp. 101–103.

In the following examples, unless indicated otherwise all parts are by weight and all temperatures in degrees centigrade.

EXAMPLE 11

Solution 2-(3,4-dichlorophenyl)-5,6,8,8A-tetrahydro-1H-imidazo-[5,1-c][1,4]thiazine-1,3(2H)-dione-7,7-dioxide: 40% dimethylformamide: 60%

The ingredients are combined and stirred to produce a solution, which can be used for low volume applications.

EXAMPLE 12

Extruded Pellet 2-(4-chloro-2-fluorophenyl)-5,6,8,8A-tetrahydro-1H-imidazo[5,1-c][1,4]thiazine-1,3(2H)-dione-7,7-dioxide: 25% anhydrous sodium sulfate: 10% crude calcium ligninsulfonate: 5% sodium alkylnaphthalenesulfonate: 1% calcium/magnesium bentonite: 59%

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Emulsifiable Concentrate 2-(3,4-dichlorophenyl)-5,6,8,8A-tetrahydro-1H-imidazo-[5,1-c][1,4]thiazine-1,3(2H)-dione-7,7-dioxide: 25% blend of oil soluble sulfonates and polyoxyethylene ethers: 4% xylene: 71%

The ingredients are combined and stirred with gentle warming to speed solution. A fine screen filter is included in packaging operation to insure the absence of any extraneous undissolved material in the product.

EXAMPLE 14

Wettable Powder 2-(4-chloro-2-fluorophenyl)-5,6,8,8A-tetrahydro-1H-imidazo[5,1-c][1,4]thiazine-1,3(2H)-dione-7,7-dioxide: 50% sodium alkylnaphthalenesulfonate: 2% sodium ligninsulfonate: 2% synthetic amorphous silica: 3% kaolinite: 43%

The ingredients are thoroughly blended, coarsely hammermilled and finally airmilled to produce particles essentially all under 15 microns. The material is reblended and sifted through a U.S.S. No. 50 sieve before packaging.

All compounds of Formulae Ia, Ib and Ic may be formulated in the same manner.

EXAMPLE 15

Granule wettable powder of Example 9: 10% attapulgite granules (U.S.S. #20–40; 0.84–0.42 mm): 90%

A slurry of wettable powder containing 50% active is sprayed on the surface of attapulgite granules in a double-cone blender. The granules are dried and packaged.

EXAMPLE 16

Aqueous Suspension 2-(4-chlorophenyl)-5,6,8,8A-tetrahydro-1H-imidazo[5,1-c][1,4]thiazine-1,3-(2H)-dione-7,7-dioxide: 60%
polyacrylic acid thickener: 0.3%
dodecylphenol polyethylene glycol ether: 0.5%
disodium phosphate: 1.0%
monosodium phosphate: 0.5%
polyvinyl alcohol: 1.0%
pentachlorophenol: 0.4%
water: 36.3%

The ingredients are ground together in a sand mill to produce particles essentially all under five microns in size.

EXAMPLE 17

High Strength Concentrate 2-(4-chlorophenyl)-5,6,8,8A-tetrahydro-1H-imidazo[5,1-c][1,4]thiazine-1,3(2H)-dione-7,7-dioxide: 98.5%
silica aerogel: 0.5%
synthetic amorphous fine silica: 1.0%

The ingredients are blended and ground in a hammer mill to produce a high strength concentrate essentially all passing a U.S.S. No. 50 sieve (0.3 mm openings). This material may then be formulated in a variety of ways.

Utility

The compounds of Formula I are useful for the pre/-postemergence control of mixed stands of weeds, such as on industrial sites, railroad and utility rights-of-way, along fences, building foundations, oil storage tanks, parking and storage lots, etc.

The amount of the compounds of Formula I to be used in any given situation will vary according to the particular end result desired, the use involved, the weed species and soil type involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to 10, per hectare. The lower rates in this range will generally be selected on lighter soils, soils low in organic matter content, or in situations where maximum persistence is not necessary.

Herbicidal activity of compounds of this invention was determined in a greenhouse test.

Test Procedure

Seeds of crabgrass (Digitaria spp.), barnyardgrass (*Echinochloa crusgalli*), wild oats (*Avena fatua*), Cassia tora morningglory (Ipomoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybeans with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

A quantitative rating was made on a scale of extending from 0 to 10. A rating of 10 means complete kill, a rating of 0 means no injury. A qualitative rating for type of injury was also made; the letter "B" denotes foliage burn, "C" indicates chlorosis/necrosis, "H" stands for formative effects, "D" means defoliation, "G" is retardation and "E" denotes emergence inhibition.

Ratings for several of the compounds tested by this procedure are recorded in Table I.

The data in Table I show that the preferred compounds of the instant invention have high herbicidal activity. Specifically, it is seen that in both pre- and postemergence applications a broad spectrum of plant species is destroyed by the instant herbicides.

TABLE I

| COMPOUND | kg/ha | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| Structure 1: O$_2$S-ring with N-C(=O)-N(=O)-aryl (4-Cl, 2-F phenyl) | 2 | 10B | 9B | 10B | 10B | 10B | 9B | 10B | 10B | 10B | 9B | 9B | 10B | 10B | 10B |
| | 0.4 | 9B | 9B | 10B | 9B | 9B | 9B | 9B | 10B | 8B | 5B | 6B | 10B | 9B | 9B |
| Structure 2: O$_2$S-ring (4-Cl phenyl) | 2 | 9B | 8B / 8D | | 7B | 8B | 5C | 10B | 9B | 2B / 3H | 2B | 6B | 6B | 6B | |
| Structure 3: O$_2$S-ring (3,4-diCl phenyl) | 2 | 9B | 5B | 4B | 7B | 3B | 3B | 7B | 6B | 2B | 1B | 3B | 7B | 2B | 3B |
| Structure 4: O$_2$S-ring (phenyl) | 2 | 1B | 2B | 1B | 1B | 1B | 0 | 0 | 1B | 0 | 0 | 0 | 1B | 0 | 1B |
| Structure 5: OS-ring (4-Cl, 2-F phenyl) | 2 | 10B | 9B | 10B | 10B | 10B | 9C | 10B | 10B | 9B | 9B | 9B | 9B | 10B | 9B |
| | 0.4 | 10B | 9B | 9B | 9B | 9B | 5B | 4B / 7H | 9B | 3B | 3B | 3B | 9B | 5B | 5B |
| Structure 6: OS-ring (4-Cl phenyl) | 2 | 9B | 8B / 8D | | 7B | 7B | 2B | 2B / 5H | 6B | 2B | 2B | 4B | 9B | 3B | 6B |

TABLE I-continued

| COMPOUND | Rate kg/ha | Bush Bean | Cotton | Sorghum | Corn | Soybean | Wheat | Wild Oats | Rice | Barnyard-grass | Crabgrass | Morning-glory | Cockle-bur | Cassia | Nutsedge |
|---|---|---|---|---|---|---|---|---|---|---|---|---|---|---|---|
|  | 2<br>0.4 | 10B<br>10B | 9B<br>9B | 10B<br>9B | 10B<br>8B | 10B | 10B | 7B<br>4B | 10B<br>4B<br>6H | 10B<br>9B | 10B<br>5B | 7B<br>4B | 9B<br>9B | 9B<br>5B | 8B<br>4B | 10B<br>7B |
| 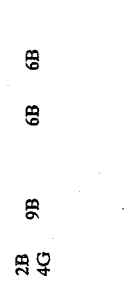 | 2 | 9B | 9B<br>8D | 10B | 5B | | 5B | 1B | 9B | | 2B | 2B | 2B<br>4G | 9B | 6B | 6B |
| 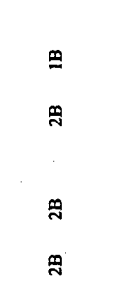 | 2 | 8B | 6B | 1B | 2B | | 1B | 1B | 1B | 6B | 2B | 1B | 2B | 2B | 2B | 1B |
|  | 2 | 5B | 6B<br>5D | 1B | 1B | | 1B | 0 | 1B | 4B | 1B | 1B | 2B | 3B | 1B | 1B |

POSTEMERGENCE

| COMPOUND | Rate kg/ha | Bush Bean | Cotton | Sorghum | Corn | Soybean | Wheat | Wild Oats | Rice | Barnyard-grass | Crabgrass | Morning-glory | Cockle-bur | Cassia | Nutsedge |
|---|---|---|---|---|---|---|---|---|---|---|---|---|---|---|---|
| 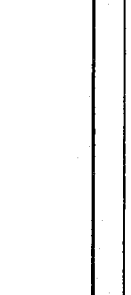 | 2 | 9B | 7B | 3B | 2B | 8B | 1B | 3B | 3B | 2B | 7B | 5B | 5B | 3B | 3B | 3B |
| 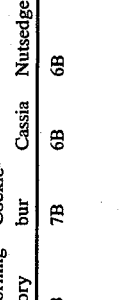 | 0.4 | | | | | | | | | | | | | | | |

TABLE I-continued

| COMPOUND | kg/ha | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| [structure: 4-Cl-phenyl, O₂S ring] | 0.4 | 6B | 4B | 1B | 1B | 0 | 1B | 8B | 0 | 1B | 4B | 2B | 1B | 1B | 1B | 1B |
| [structure: 4-Cl-2-F-phenyl, S ring] | 0.4 | 9B | 10B | 6B | 7B | 9B | 3B | 4B | 6B | 9B | 10B | 10B | 10B | 8B | 10B | 8B |
| [structure: 4-Cl-2-F-phenyl, O₂S ring] | 0.4 | 9B | 8B 7D | 6B | 4B 7B | 2B | 5B 8H | 6B | 9B | 6B | 9B | 9B | 8B | 8B | 6B | 2G |

POST EMERGENCE

| COMPOUND | kg/ha | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| [structure: 4-Cl-phenyl, S ring with Cl] | 2 | 10B | 9B | 10B | 10B | 10B | 5B | 10B | 10B | 10B | 9B | 8B | 10B | 10B | 10B | 5B |
| [structure: 4-Cl-2-F-phenyl, S ring with Cl] | 2 | — | — | 10B | 6B | 10B | 9B | 9B | 9B | | | | | | | |
| [structure: 4-Cl-2-F-phenyl, OS ring with Cl] | 2 | — | — | 10B | 10B | 10B | 4B 7G | 10B | 10B | 6B 9H 4B 7H | 6B 9H 4B 6H | 6B 9H 4B | 9B | 9B | 10B | 9B |
| | 0.4 | | | | | | | | | | | | | 8C | | 8B |

TABLE I-continued

| COMPOUND | kg/ha | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
| 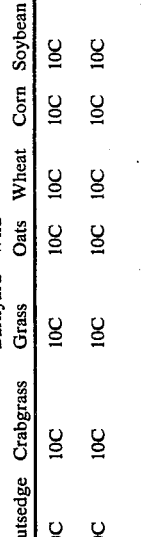 | 2 | 10B | 9B | 9B | 7C | 9B | 9B | 3B 8H | 5B 9H | 5B 9H 3B 7H | 9B | 9B | 5B 9H |
|  | 0.4 |  | 9B | 9B | 1B 5G |  |  | 4B 8H | 5B 4B 6H | 3B 7H | 9B | 5B 8G | 5B 9H |
| 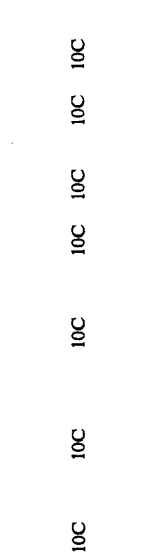 | 2 | 10B | 5B | — | 1B 5C 0 | 4B 9H 2B 9H | 5B 9H 7B | 4B 7H 2B | 5B 2B | 4B 2B | 9B 7B | 4B 8G 7B | 4B 7H 4B |
|  | 0.4 | 8B | 3B | 1B 6G |  |  |  |  |  |  |  |  |  |
| 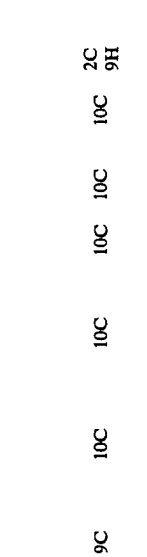 | 2 | 2B | 2B | 1B | 1B 5C | 4B 9H | 5B 8H | 4B 7H | 3B | 1B 4C | 4B 8G | 4B 7G | 5B 9H |

PRE-EMERGENCE

| COMPOUND | kg/ha | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
|  | 2 | 10C | 10C | 10C | 10C | 10C | 10C | 10C | 10C | 10C | 10C | 10C | 10C |
|  | 0.4 | 10C | 10C | 10C | 10C | 10C | 10C | 10C | 10C | 10C | 10C | 10C | 10C |
|  | 2 | 10C | 10C | 10C | 10C | 10C | 10C | 10C | 10C | 10C | 10C | 10C | 10C |
|  | 2 | 10C | 10C | 10C | 9C | 10C | 10C | 10C | 10C | 10C | 10C | 10C | 10C |
|  | 2 | 10C | 10C | 10C | 10C | 10C | 10C | 10C | 10C | 10C | 2C 9H | 9C | 10C |

TABLE I-continued

| Structure | | | | | | | | | | | | | |
|---|---|---|---|---|---|---|---|---|---|---|---|---|---|
| phenyl, SO₂ ring | 2 | 10C | 10C | 10C | 10C | 10C | 10C | 10C | 10C | 10C | 10C | 0 | 0 |
| 4-Cl-2-F phenyl, SO ring | 2 | 10C | 10C | 10C | 10C | 10C | 10C | 10C | 10C | 10C | 10C | 0 | 0 |
|  | 0.4 | 10C | 10C | 10C | 10C | 10C | 10C | 5C 9H | 9C | 9C | 10C | 0 | 0 |
| 4-Cl phenyl, SO ring | 2 | 10C | 10C | 9C | 10C | 10C | 10C | 10C | 10C | 10C | 10C | 0 | 0 |
| 4-Cl-2-F phenyl, S ring | 2 | 10C | 10C | 10C | 10E | 9C | 10C | 10C | 10C | 10C | 10C | 0 | 0 |
|  | 0.4 | 10C | 10C | 7C | | 10C | 10C | 10C | 10C | 9C | 10C | 0 | 0 |
| 4-Cl phenyl, S ring | 2 | 10C | 10C | 9C | 10C | 10C | 9C | 9C | 10C | 9C | 9C | 0 | 0 |
| 3,4-diCl phenyl, S ring | 2 | 1C 9G | 1C 7G | 1C 5G | 2C | 10C | 9C | 4C 8H | 2C 6H | 9C | 7C | 0 | 0 |

TABLE I-continued
| COMPOUND | Rate kg/ha | Sorghum | Corn | Soybean | Wheat | Wild Oats | Rice | Barnyard-Crabgrass | Morning-glory | Morning-bur | Cockle-Cassia | Nutsedge |
|---|---|---|---|---|---|---|---|---|---|---|---|---|
| PREEMERGENCE |
| 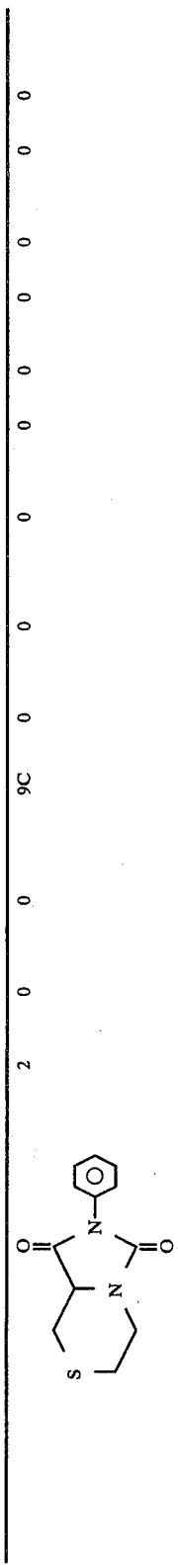 | 2 | 9C | 9C 2H | 2C 5G | 9C | 9C | 9C | 9C | 9C | 10C | 10C | 9C | 6C |
| (4-Cl-phenyl, S) | 0.4 | 8C | 0 | 5C | 7C | 8C | 8C | 9C | 9C | 6C | 7C | 10C | 0 |
| (4-Cl-phenyl, OS) | 0.4 | 10C | 5C 9H | 3C 9H | 9C | 9C | 9C | 9C | 10C | 9C | 9C | 10C | 8C |
| (4-Cl-phenyl, O₂S) | 0.4 | 9C | 3C 9H | 5C 9H | 9C | 9C | 8C | 4C 9H | 2C 9H | 10C | 10C | 10C | 1C 5G |
| (4-Cl-2-F-phenyl, S) | 0.4 | 10C | 9C | 10C | 10C | 10C | 10C | 10C | 10C | 10C | 10C | 10C | 10C |
| (4-Cl-2-F-phenyl, O₂S) | 0.4 | | | | | | | | | | | | |
PRE-EMERGENCE TABLE I-continued

| COMPOUND | kg/ha | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
| [structure: 4-Cl-phenyl, S] | 2 | 2C 9G | 2C 9G | 10C | 5C | 9H | 5C | 9C | 9C | 3C | 9H | 9C | 10C |
| [structure: 4-Cl-2-F-phenyl, S] | 2 | 10C | 9C | | | | 9H | | | 9H | | | 9H |
| [structure: 4-Cl-2-F-phenyl, OS] | 2 | 10C | 9C | 10C | 9C | 10C | 10C | 10C | 10C | 9H | 9H | 9C | 10C |
| | 0.4 | 10C | — | 10C | 9C | 10C | 10C | 10C | 9C | 9H | 9H | 9C | 9H |
| [structure: 4-Cl-2-F-phenyl, O₂S] | 2 | 10C | 10C | 10C | 9C | 10C | 10C | 10C | 10C | 9H | 9C | 9C | 10C |
| | 0.4 | 10C | 10C | 10C | 9C | 10C | 10C | 10C | 10C | 9H | 10H | 9C | 10C |
| [structure: 2-OCH₃-4,5-diCl-phenyl, S] | 2 | 2C 9H 1C 6G | 3H | 1C 4H | 8C | 9H | 9C | 10C 9H | 9C 5C 8H | 2C 9H 2C 7H | 3C 6G 0 | 10C 10C | 9C 8C 8H |
| | 0.4 | | 3H | | 1C | 5H | 4C 8H | 5C 9H | 5C 8H | | | | |
| [structure: 2-OCH₃-4,5-diCl-phenyl, O₂S] | 2 | 10C | 3C 9H | 10C | 6C | 9H | 10H | 10C | 10C | 9C | 10C | 10C | 9H |

I claim:
1. A compound of the formula:

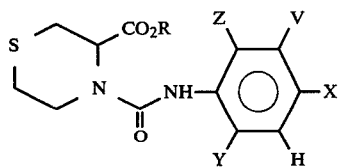

where
X is hydrogen, fluorine, chlorine, bromine, cyano, methyl, methoxy or nitro;
Y is hydrogen, fluorine, chlorine or methyl;
Z is hydrogen, fluorine or methyl;
V is hydrogen, fluorine, chlorine or OR; and
R is propargyl or alkyl of 1 to 4 carbon atoms with the proviso that when V is other than H, at least one X, Y and Z must be other than H.

2. A compound of claim 1 wherein X is fluorine, chlorine, bromine, or cyano.

3. A compound of claim 1 wherein Y is hydrogen, fluorine, or chlorine.

4. A compound of claim 1 wherein Z is hydrogen or fluorine.

5. A compound of claim 1 wherein V is hydrogen, fluorine, chlorine, or OR where R is alkyl of 1 to 3 carbon atoms.

6. A composition for the control of undesirable vegetation consisting essentially of a compound of claim 1 and at least one of (a) a surface-active agent and (b) a solid or liquid diluent.

7. A composition for the control of undesirable vegetation consisting essentially of a compound of claim 2 and at least one of (a) a surface-active agent and (b) a solid or liquid diluent.

8. A composition for the control of undesirable vegetation consisting essentially of a compound of claim 3 and at least one of (a) a surface-active agent and (b) a solid or liquid diluent.

9. A composition for the control of undesirable vegetation consisting essentially of a compound of claim 4 and at least one of (a) a surface-active agent and (b) a solid or liquid diluent.

10. A composition for the control of undesirable vegetation consisting essentially of a compound of claim 5 and at least one of (a) a surface-active agent and (b) a solid or liquid diluent.

11. A method for the control of undesirable vegetation comprising applying to the locus of such undesirable vegetation a herbicidally effective amount of a compound of claim 1.

12. A method for the control of undesirable vegetation comprising applying to the locus of such undesirable vegetation a herbicidally effective amount of a compound of claim 2.

13. A method for the control of undesirable vegetation comprising applying to the locus of such undesirable vegetation a herbicidally effective amount of a compound of claim 3.

14. A method for the control of undesirable vegetation comprising applying to the locus of such undesirable vegetation a herbicidally effective amount of a compound of claim 4.

15. A method for the control of undesirable vegetation comprising applying to the locus of such undesirable vegetation a herbicidally effective amount of a compound of claim 5.

* * * * *